United States Patent [19]

Clark et al.

[11] Patent Number: 5,220,092
[45] Date of Patent: Jun. 15, 1993

[54] PROCESS FOR THE PREPARATION OF ALKENES

[75] Inventors: David M. Clark; Petrus J. J. Tromp; Peter Arnoldy, all of Amsterdam, Netherlands

[73] Assignee: Shell Oil Company, Houston, Tex.

[21] Appl. No.: 894,136

[22] Filed: Jun. 4, 1992

[30] Foreign Application Priority Data

Jun. 25, 1991 [GB] United Kingdom ............. 9113686

[51] Int. Cl.$^5$ .................. C07C 5/333; C07C 5/327
[52] U.S. Cl. ............................ 585/661; 585/654
[58] Field of Search ........................ 585/661, 654

[56] References Cited

U.S. PATENT DOCUMENTS

| | | |
|---|---|---|
| 2,570,067 | 10/1951 | Myers . |
| 2,576,034 | 11/1951 | Myers . |
| 2,638,455 | 5/1953 | Pitzer . |
| 2,814,650 | 11/1957 | Clark . |
| 3,228,992 | 1/1966 | Myers . |
| 3,711,569 | 1/1973 | Tschopp et al. . |
| 4,108,913 | 8/1978 | Spoerke et al. .......... 585/663 |
| 4,607,129 | 8/1986 | Lee . |
| 4,644,089 | 2/1987 | Lee . |

*Primary Examiner*—Anthony McFarlane
*Assistant Examiner*—Nhat D. Phan

[57] ABSTRACT

A process for the preparation of alkenes by contacting a feed containing one or more $C_2$–$C_{10}$ alkanes at an elevated temperature with a catalyst containing 1–15% w vanadia, calculated as divanadium pentoxide relative to the weight of the catalyst, on a refractory support, where the feed is contacted with the catalyst at a temperature of 600° C. or above during less than 4 seconds.

13 Claims, No Drawings

PROCESS FOR THE PREPARATION OF ALKENES

FIELD OF THE INVENTION

This invention relates to a process for the preparation of alkenes by contacting a feed containing one or more $C_2-C_{10}$ alkanes at elevated temperature with a catalyst comprising vanadia on a refractory support.

BACKGROUND OF THE INVENTION

In traditional hydrocarbon processes for preparing alkenes the alkane(s) is/are dehydrogenated to one or more alkenes with concomitant formation of hydrogen. There are several problems associated with these processes. For example, due to the chemical equilibrium between the alkane(s), alkene(s) and hydrogen it is in general not possible to convert the alkane(s) completely into the desired alkene(s). The selectivity to the desired alkene(s) may be low because cracked products and coke may be formed at the expense of starting material and/or reaction product, in particular in the dehydrogenation of unbranched alkanes.

According to the disclosures in, inter alia, U.S. Pat. Nos. 2,570,067, 2,638,455, 2,576,034 and 3,711,569, it is preferred to employ in the vanadia catalyzed dehydrogenation reactions catalysts which have a relatively high vanadia content, for example above 15% w, calculated as divanadium pentoxide, relative to the weight of the catalyst. In other documents, inter alia in U.S. Pat. Nos. 2,814,650, 3,228,992, U.S. Pat. No. 4,607,129 and 4,644,089, a preference for catalyst with a lower vanadia content is expressed. Likewise, the temperature at which the dehydrogenation reactions can be carried out may vary between wide limits, for example, from 400° C. to 700° C.

U.S. Pat. No. 4,607,129 discloses a process for the preparation of alkenes. A feed containing one or more $C_2-C_{10}$ alkanes is contacted at an elevated temperature with a catalyst containing 1-15% w vanadia, calculated as divanadium pentoxide relative to the weight of the catalyst, on a refractory support. In the process the most preferred temperature range for contacting the feed with the catalyst amounts to from 482° to 593° C. and the most preferred range of reaction times amounts to from 4 to 8 seconds. In the processes referred to, the yield of the desired alkene(s) leaves room for improvement. Therefore, it would be advantageous to provide a dehydrogenation process with an improved yield of alkenes.

SUMMARY OF THE INVENTION

It has now unexpectedly been found that in the dehydrogenation of an alkane in the presence of a catalyst of vanadia on a refractory support a substantially improved yield of alkene can be accomplished by applying a high reaction temperature (i.e. 600° C. or above) combined with a short residence time of the alkane in the reactor (i.e. below 4 seconds), provided that the catalyst has a relatively low content of vanadia (i.e. 1-15% w calculated as divanadium pentoxide, relative to the weight of the catalyst). For example, by applying these conditions a yield of propene of more than 40% can be achieved in the dehydrogenation of propane and a yield of more than 50% can be achieved in the dehydrogenation of isobutane, whereas the conditions exemplified in U.S. Pat. No. 4,607,129, as far as they concern the dehydrogenation of propane and isobutane, do not provide yields of propene and isobutene which are higher than 30% and 25%, respectively.

The improvement in the dehydrogenation of unbranched alkanes is particularly surprising as unbranched alkanes are more difficult to dehydrogenate in a selective way than branched alkanes. Accordingly, the invention relates to a process for the preparation of alkenes by contacting a feed containing one or more $C_2-C_{10}$ alkanes at an elevated temperature with a catalyst containing 1-15% w vanadia, calculated as divanadium pentoxide relative to the weight of the catalyst, on a refractory support, wherein the feed is contacted with the catalyst at a temperature of 600° C. or above during less than 4 seconds.

DETAILED DESCRIPTION OF THE INVENTION

Preferably the catalyst contains from 3 to 12% w and, in particular, from 4 to 9% w vanadia calculated as divanadium pentoxide, relative to the weight of the catalyst. Very good results can be obtained with catalysts which contain about 6.3% w vanadia.

The catalysts optionally contain in addition to vanadia, one or more compounds comprising one or more phosphorus compounds or, preferably, one or more (earth-)alkali metal compounds. Preferably the (earth-)alkali metal(s) is/are lithium, sodium, potassium and/or, in particular, cesium. Eligibly, the quantity of (earth-)alkali metal present in the catalyst amounts from 0.05 to 0.5 gram equivalent/kg catalyst, preferably from 0.1 to 0.3 gram equivalent/kg catalyst. Phosphorus compounds are preferably present in such quantities that the catalyst contains from 0.05 to 3 gram atom phosphorus/kg catalyst, and preferably from 0.1 to 2 gram atom phosphorus/kg catalyst.

The refractory support may be of any available type, such as supports comprising magnesium oxide, titanium oxide, magnesium aluminate or aluminium phosphate. Preferred refractory support comprise silica, whereas alumina supports are the most preferred refractory supports.

The alumina supports are preferably obtained from porous alumina which can be any of the variety of available aluminas, such as alumina hydrates, alumina gel and activated alumina. Very preferable aluminas are found to be those which have a surface area ranging from 10 $m^2/g$ to 500 $m^2/g$, preferably from 50 $m^2/g$ to 400 $m^2/g$. In a preferred embodiment the alumina support is gamma alumina.

The catalyst may be prepared by impregnating or otherwise providing the refractory support with the desired quantity of vanadia and, optionally, the (earth-)alkali metal compound(s) or phosphorus compound(s) referred to hereinbefore. Various sources of vanadia for impregnating the catalyst support are known in the art, such as vanadium(V) and vanadium(IV) compounds, for example, divanadium pentoxide, vanadyl sulphate, ammonium metavanadate and sodium metavanadate, which compounds are preferably used in the form of an aqueous solution. Very good results can be obtained by impregnating with ammonium polyvanadate dissolved in aqueous oxalic acid. The (earth-)alkali metal compound(s) may be introduced by impregnating the refractory support with an aqueous solution of the nitrate, the hydroxide and/or the carbonate of the (earth-)alkali metal(s) or any other (earth-)alkali metal compound(s).

Compounds of phosphorus which can be used in the impregnation of the refractory support may be inorganic or organic compounds. Preferable inorganic phosphorus containing compounds are phosphoric acids and their alkali metal and ammonium salts. After the impregnation, the refractory support is preferably dried, typically at a temperature above 60° C., especially between 100° and 150° C., for example at about 120° C., and calcined, preferably by heating in an oxygen containing atmosphere at a temperature in the range of from 300° to 800° C., typically in the range of from 400° to 600° C. Good results can be obtained by calcining in air at 450° C. for 1 hour. The vanadium and the (earth-)alkali metal or phosphorus compound(s) may be supplied simultaneously, by impregnating the support with a solution comprising the (earth-)alkali metal or phosphorus compound(s) and the source of vanadia or by impregnating the support with an (earth-)alkali metal containing vanadium compound, for example sodium orthovanadate or cesium metavanadate. Very good results can also be obtained by carrying out the impregnation in two steps, viz. by first impregnating with the (earth-)alkali metal compound, followed, after removal of water from the support, by impregnation with the source of vanadia.

The catalyst may be brought into any appropriate shape prior to the impregnation, or after the impregnation. Various techniques for shaping the catalyst are available in the art, such as extrusion and compression moulding. In the present process very good results can be obtained with catalysts which are prepared by impregnating an alumina extrudate, as well as with catalysts which are prepared by impregnating a spray-dried alumina powder.

Before using the catalyst in the process of the invention, the catalyst may be subjected to heat, preferably at the same or approximately the same temperature as the temperature employed in the dehydrogenation process, in the presence of an inert gas, such as argon or nitrogen, or in the presence of a reactive gas, such as hydrogen or ammonia. A freshly prepared catalyst may be subjected to such a heat treatment, as well as a catalyst which is obtained from a regeneration step, as described hereinafter.

In the process of the invention a feed containing one or more $C_2$-$C_{10}$ alkanes, preferably $C_2$-$C_5$ alkanes, is converted into a product containing alkenes. Usually monoalkenes are formed. When the feed comprises acyclic alkanes having a sufficiently long chain of carbon atoms, dialkenes and/or cyclic products may be formed as well. A particularly preferable feed contains alkanes which have been prepared in a Fischer-Tropsch synthesis. Preferably the feed contains propane and/or isobutane.

The present process is preferably carried out in a continuous mode of operation, preferably using a fluidized bed or a moving packed catalyst bed. The bed of catalyst may move upwards or downwards.

In the present process the feed is contacted with the catalyst during less than 4 seconds, preferably less than 3 seconds. Preferably the minimum residence time of the feed in contact with the catalyst is 0.01 seconds, preferably 0.02 seconds. Very good results are obtainable with a process in which the feed is contacted with the catalyst during 0.02 to 2 seconds. To a skilled person it will immediately be clear that the residence time required for a certain conversion level may depend, among other things, from the density of the catalyst particles in a reaction zone. When using a packed catalyst bed, having in general a higher density than a fluidized catalyst, a lower residence time may be employed than when using the fluidized catalyst. In a continuous process the residence time is usually expressed in a gas hourly space velocity (GHSV) which is in the present process typically above 2000 Nl/(l.h), preferably the GHSV is below 15000 Nl/(l.h).

The temperature at which the feed is contacted with the catalyst should be 600° C. or higher, preferably higher than 625° C. and in particular higher than 650° C. The temperature is preferably kept below 750° C., in particular below 725° C., in order to limit the formation of coke.

The pressure in the present process can be varied within wide ranges. It is preferred that the pressure is such that at the prevailing temperature the feedstock is substantially in its gaseous phase. Then it is easier to achieve the short residence times envisaged. Hence, the pressure is preferably in the range of from 0.1 to 5 bar. This can be advantageous since no expensive compressors are necessary. Other gaseous materials may be present during the conversion, such as steam and/or nitrogen.

In oxidative dehydrogenation processes, known in the art, the feed comprises oxygen, in addition to the alkane(s). In such processes the hydrogen, which is formed as a result of the dehydrogenation of the alkane(s), will be converted into water. As hydrogen is a valuable material, the process of the invention is intended to be carried out substantially in the absence of oxygen. During the process some coke may be formed on the catalyst. Therefore, it could be advantageous to regenerate the catalyst in a regeneration step, preferably, by subjecting the catalyst after having been contacted with the feedstock to a treatment with an oxidizing gas, such as air. A continuous regeneration, similar to the regeneration carried out in a fluidized catalytic cracking reaction, is specially preferred.

If coke formation does not occur at a rate which is too high it would be possible to arrange for a process in which the residence time of the catalyst particles in the reaction zone is longer than the residence time of the feedstock in the reaction zone. Of course, the residence time of the feedstock should be less than 4 seconds. Preferably the residence time of the catalyst is from 1 to 50 times the residence time of the feedstock.

While the catalyst/feedstock weight ratio is not critical, it is preferred that this weight ratio varies from 1 to 300 kg or more catalyst per kg of feedstock. Preferably the catalyst/feedstock weight ratio is from 20 to 120:1.

The alkenes obtained in the present process may be recovered and purified by any known technique, such as distillation. Unconverted starting alkane(s) may be isolated as well and, if desired, fed to a subsequent dehydrogenation, optionally, after combining with fresh feed.

The present invention will be further illustrated by means of the following illustrative embodiments which are not intended to limit the scope of the invention in any way.

ILLUSTRATIVE EMBODIMENTS 1-8

Catalyst Preparation

Samples of a gamma-alumina support (crushed extrudates, particle size 2.1-3 mm, surface area 192 $m^2/g$, pre-calcined at 750° C. during 16 hours) were impregnated with an aqueous solution of ammonium polyvanadate in oxalic acid by mixing a sample of the support with a quantity of the aqueous solution which is sufficient to fill the pores of the support, the quantity of vanadium present in the solution being the quantity to be supplied to the support. Subsequently, the mixtures were dried and calcined in air.

For example, a catalyst containing 6.3% w vanadia, calculated as vanadium pentoxide relative to the weight of the catalyst, was prepared as follows. Oxalic acid (68.53 g) was added in small portions to a stirred suspension of 32.09 g ammonium polyvanadate in 200 ml demineralized water while the temperature of the mixture was kept at 70°–80° C. After having obtained a clear solution, additional demineralized water was added to adjust the volume to 566 ml. The solution thus obtained was added in small portions to 435 g of a gamma-alumina support having a pore volume of 1.3 ml/g. During the addition the support was kept in motion to ensure that all support particles were wetted. About 90 minutes after the addition of the last portion of solution the support was dried by heating in an oven at 120° C. for 4 hours and subsequently calcined by heating at 450° C. for 1 hour.

In illustrative embodiment 1, the support was impregnated with aqueous oxalic acid without a vanadium compound being present. For each of the catalysts prepared the contents of vanadia, calculated as divanadium pentoxide, are given in Table 1.

Dehydrogenation of Propane

A quartz tubular reactor (2 mm diameter) was charged with a 100 mg sample of one of the catalysts obtained. The catalyst bed thus formed was heated at 700° C. in a flow of 2.14 Nl argon/h. At certain intervals of time the flow of argon was interrupted by feeding a pulse of propane (2.4 Nml at the same flow rate as the argon flow. From the composition of the gasses leaving the reactor, as measured by gas-liquid chromatography, the conversion of propane and the selectivity and the yield of propene were calculated. The residence time of the gas in contact with the catalyst was calculated, taking into account the temperature and the average pressure (about 1.4 bar) of the reaction mixture in the reactor. The residence time was found to be approximately 0.1 s. The results of the fifth pulse in each of the Illustrative Embodiments 1–8 are given Table 1.

TABLE 1

| Illust. Embod. | Content of vanadia[1] % w | Propane conversion % mol | Selectivity to propene % mol | Yield of propene % mol |
| --- | --- | --- | --- | --- |
| 1[2] | 0 | 17 | 84 | 14 |
| 2 | 1.8 | 32 | 88 | 28 |
| 3 | 4.5 | 49 | 84 | 41 |
| 4 | 6.3 | 52 | 82 | 43 |
| 5 | 8.9 | 49 | 83 | 41 |
| 6 | 13 | 27 | 84 | 23 |
| 7[2] | 18 | 14 | 85 | 12 |
| 8[2] | 36 | 18 | 87 | 16 |

[1]Calculated as divanadium pentoxide, relative to the weight of the catalyst.
[2]For comparison, not according to the invention.

ILLUSTRATIVE EMBODIMENTS 9–10

The catalyst preparation and the dehydrogenation of propane according to 2–8 were substantially repeated but with the difference that a silica support (crushed extrudates, surface area 351 m²/g) was used instead of a gamma-alumina support. For each of the catalysts prepared the contents of vanadia, calculated as divanadium pentoxide, and the results of the fifth pulse are given Table 2.

TABLE 2

| Illust. Embod. | Content of vanadia[1] % w | Propane conversion % mol | Selectivity to propene % mol | Yield of propene % mol |
| --- | --- | --- | --- | --- |
| 9 | 3.6 | 23 | 91 | 21 |
| 10 | 8.9 | 22 | 92 | 20 |

[1]Calculated as divanadium pentoxide, relative to the weight of the catalyst.

ILLUSTRATIVE EMBODIMENT 11

Dehydrogenation of Propane

The dehydrogenation of propane according to Illustrative Embodiment 3 was substantially repeated but with the following differences.

1. A 75 mg sample of the catalyst was used instead of a 100 mg sample,
2. The catalyst bed was heated at 600° C. instead of at 700° C., and
3. After the 6$^{th}$ pulse, the 9$^{th}$ pulse and the 14$^{th}$ pulse the temperature was increased by 50° C. to 650° C., 700° C. and 750° C., respectively.

The results of the 6$^{th}$ pulse, the 9$^{th}$ pulse, the 14$^{th}$ pulse and the 17$^{th}$ pulse are given Table 3.

TABLE 3

| Pulse | Temperature °C. | Propane conversion, % mol | Selectivity to propene % mol | Yield of propene % mol |
| --- | --- | --- | --- | --- |
| 6 | 600 | 9 | about 100 | 9 |
| 9 | 650 | 22 | 95 | 20 |
| 14 | 700 | 42 | 87 | 36 |
| 17 | 750 | 54 | 64 | 35 |

ILLUSTRATIVE EMBODIMENT 12–19

Dehydrogenation of Propane

The dehydrogenation of propane according to Illustrative Embodiment 4 was substantially repeated but with the following differences.

1. Variable quantities of the catalyst were used, as indicated in Table 4, and
2. The catalyst bed was heated in Illustrative Embodiments 12–14 at a temperature of 650° C. and in Illustrative Embodiments 15–19 at a temperature of 700° C.

The average pressure amounted to about 1.2–1.4 bar. The results of the 5th pulse in each of Illustrative Embodiments 12–19 are given Table 4.

TABLE 4

| Illust. Embod. | Quantity of catalyst mg | Flow rate Nl/h | Residence time s | Propane conversion % mol | Selectivity to propene % mol | Yield of propene % mol |
| --- | --- | --- | --- | --- | --- | --- |
| 12[1] | 100 | 2.14 | 0.049 | 28 | 90 | 25 |
| 13[1] | 300 | 2.14 | 0.14 | 52 | 84 | 44 |
| 14[1] | 300 | 1.07 | 0.27 | 66 | 66 | 44 |
| 15[2] | 50 | 2.14 | 0.022 | 27 | 91 | 25 |
| 16[2] | 100 | 2.14 | 0.046 | 47 | 82 | 39 |
| 17[2] | 300 | 2.14 | 0.13 | 81 | 56 | 45 |
| 18[2] | 250 | 1.07 | 0.21 | 86 | 44 | 38 |
| 19[2] | 333 | 1.07 | 0.29 | 87 | 36 | 31 |

[1]Reaction temperature 650° C.
[2]Reaction temperature 700° C.

ILLUSTRATIVE EMBODIMENT 20-25

Catalyst Preparation

Samples of a gamma-alumina support (crushed extrudates, particle size 2.1-3 mm, surface area 192 m²/g were impregnated with an aqueous solution of ammonium polyvanadate oxalic acid and a compound selected from lithium hydroxide, potassium nitrate, cesium hydroxide and phosphoric acid and subsequently dried and calcined by the procedures described for Illustrative Embodiments 2-8. The catalysts thus prepared contained 6.3% w vanadia, calculated as divanadium pentoxide and their contents of alkali metal or phosphorus are given in Table 5.

Dehydrogenation of Propane

A quartz tubular reactor (2 mm diameter) was charged with a 300 mg sample of one of the catalysts obtained, except for Illustrative Embodiments 24 and 25, in which a 100 mg sample was used. The catalyst bed thus formed was heated at 700° C. in a flow of 2.14 Nl argon/h. At certain intervals of time the flow of argon was interrupted by feeding a pulse of propane (2.4 Nml) at a the same flow rate. From the composition of the gasses leaving the reactor, as measured by gas-liquid chromatography, the conversion of propane and the selectivity and the yield of propene were calculated. The residence time of the gas in contact with the catalyst was calculated, taking into account the temperature and the average pressure of the reaction mixture in the reactor. In Illustrative Embodiments 20-23 the residence time amounted to approximately 0.1 s, in Illustrative Embodiments 24 and 25 the residence time was approximately 0.04 s. The results calculated for the fifth pulse in each of the Illustrative Embodiments 20-25 are given Table 5.

TABLE 5

| Illust. Embod. | Alkali metal (content. % w) | Propane conversion % mol | Selectivity to propene % mol | Yield of propene % mol |
|---|---|---|---|---|
| 20[1] | Lithium (0.09) | 77 | 63 | 49 |
| 21[1] | Potassium (0.5) | 72 | 70 | 50 |
| 22[1] | Potassium (1.0) | 56 | 77 | 43 |
| 23[1] | Cesium (1.7) | 69 | 76 | 52 |
| 24[2] | [3](1.0) | 52 | 81 | 42 |
| 25[2] | [3](2.0) | 44 | 86 | 38 |

[1] Residence time: about 0.1 s.
[2] Residence time: about 0.04 s.
[3] Phosphorus compound was present instead of an alkali metal compound; in brackets: phosphorus content.

ILLUSTRATIVE EMBODIMENT 26 AND 27

Dehydrogenation of Isobutane

A quartz tubular reactor (2 mm diameter) was charged with a quantity of the catalyst obtained in the catalyst preparation of Illustrative Embodiment 23. In Illustrative Embodiment 26 a 600 mg sample was used, whereas in Illustrative Embodiment 27 a 300 mg sample was used. The catalyst bed thus formed was heated in a flow of argon in Illustrative Embodiment 26 at 600° C. and in Illustrative Embodiment 27 at 650° C. At certain intervals of time the flow of argon was interrupted by feeding a pulse of isobutane (2.4 Nml) at the same flow rate as the flow of argon. From the composition of the gasses leaving the reactor, as measured by gas-liquid chromatography, the conversion of isobutane and the selectivity and the yield of isobutene were calculated. The residence time of the gas in contact with the catalyst was calculated, taking into account the temperature and the average pressure of the reaction mixture in the reactor of 1.1-1.5 bar. The results of the fifth pulse are given in Table 6.

TABLE 6

| Illust. Embod. | Quantity of Catalyst mg | Flow rate Nl/h | Residence time s | Isobutane conversion % mol | Selectivity to isobutene % mol | Yield of isobutene % mol |
|---|---|---|---|---|---|---|
| 26[1] | 600 | 0.48 | 1.0 | 61 | 85 | 52 |
| 27[2] | 300 | 0.75 | 0.30 | 71 | 78 | 55 |

[1] Reaction temperature 600° C.
[2] Reaction temperature 650° C.

What is claimed is:

1. A process for the preparation of alkenes comprising contacting a feed containing at least one $C_2$ to $C_{10}$ alkane with a catalyst consisting essentially of from 3% wt vanadia to 12% wt vanadia, calculated as divanadium pentoxide relative to the weight of the catalyst, on an alumina support, wherein the feed is contacted with the catalyst at a temperature of at least 600° C. for less than 4 seconds.

2. The process as claimed in claim 1 wherein the catalyst contains from 4% wt vanadia to 9% wt vanadia calculated as divanadium pentoxide, relative to the weight of the catalyst.

3. The process as claimed in claim 1 wherein the alumina support is gamma alumina.

4. The process as claimed in claim 1 wherein the feed contains alkanes which have been prepared in a Fischer-Tropsch synthesis.

5. The process as claimed in claim 1 wherein the feed contains propane, isobutane, or admixtures thereof.

6. The process as claimed in claim 2 wherein the reaction temperature is from 625° C. to 750° C.

7. The process according to claim 2 wherein the fed is contacted with the catalyst for a contact time of 0.30 s.

8. The process as claimed in claim 6 wherein the reaction temperature is from 650° C. to 725° C.

9. The process as claimed in claim 6 wherein the feed is contacted with the catalyst from 0.01 seconds to 3 seconds.

10. The process as claimed in claim 9 wherein the feed is contacted with the catalyst from 0.02 seconds to 2 seconds.

11. The process as claimed in claim 6 wherein the process is a continuous process wherein a gas hourly space velocity of the alkanes is from 2000 Nl/(l.h) to 15000 Nl/(l.h).

12. A process for the preparation of alkenes comprising contacting a feed comprising at least one $C_2$ to $C_{10}$ alkane prepared in a Fischer-Tropsch synthesis wherein said alkanes have a gas hourly space velocity from 2000 Nl/(l.h) to 15000 Nl/(l.h) with a catalyst consisting essentially of from 4% wt vanadia to 9% wt vanadia, calculated as divanadium pentoxide relative to the weight of the catalyst, on a gamma alumina refractory support, wherein the feed is contacted with the catalyst at a temperature of from 650° C. to 725° C. for from 0.02 seconds to 2 seconds.

13. The process according to claim 12 wherein the feed is contacted with the catalyst for a contact time of 0.30 s.

* * * * *